(12) United States Patent
Matsumoto et al.

(10) Patent No.: US 6,641,700 B1
(45) Date of Patent: Nov. 4, 2003

(54) PURIFYING APPARATUS POSSESSING VAPOR DISPERSING DEVICE

(75) Inventors: Hajime Matsumoto, Himeji (JP); Takeshi Nishimura, Himeji (JP); Yukihiro Matsumoto, Kobe (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/519,383

(22) Filed: Mar. 3, 2000

(30) Foreign Application Priority Data

Mar. 9, 1999 (JP) .......................... 11-061785

(51) Int. Cl.[7] .................. B01D 3/34; C07C 51/44
(52) U.S. Cl. .................. 202/158; 202/182; 202/201; 562/600; 203/8; 203/49; 203/DIG. 21
(58) Field of Search ............... 203/100, 8, DIG. 21, 203/DIG. 25, 9, 98, 49; 562/600; 202/158, 182, 201; 159/26.2, 16.1

(56) References Cited

U.S. PATENT DOCUMENTS

| 3,988,213 A | * 10/1976 | Yoshida et al. .............. 203/9 |
| 4,379,736 A | 4/1983 | Kendall et al. |
| 4,490,215 A | * 12/1984 | Bannon ..................... 196/111 |
| 5,578,173 A | 11/1996 | Toot, Jr. et al. |
| 6,034,288 A | * 3/2000 | Scott et al. ................ 570/102 |
| 6,294,056 B1 | * 9/2001 | Matsumoto et al. ........ 202/158 |
| 6,348,135 B1 | * 2/2002 | Nakahara et al. ............ 203/49 |

FOREIGN PATENT DOCUMENTS

| GB | 1265738 | * 3/1972 |
| JP | A-51-2675 | 6/1974 |
| JP | A-3-196801 | 8/1991 |

OTHER PUBLICATIONS

Shah, "Troubleshooting distillation columns", Chemical Engineering, Jul. 31, 1978, pp. 71–78.*

* cited by examiner

Primary Examiner—Virginia Manoharan
(74) Attorney, Agent, or Firm—Mathews, Collins, Shepherd & McKay, P.A.

(57) ABSTRACT

A purifying apparatus characterized by being equipped with a vapor dispersing device possessing in a vapor inlet part owned by the apparatus on the lateral inside thereof an opening part facing downward from the horizontal direction and a horizontal projected cross section area in the range of 10–40% of the cross section area of said apparatus. In consequence of the incorporation of the vapor dispersing device according to this invention, the drift of the gas is repressed, the efficiency of separation is improved, and the possible polymerization of a compound under treatment in the lower part of the column is prevented.

12 Claims, 8 Drawing Sheets

PURIFYING APPARATUS POSSESSING VAPOR DISPERSING DEVICE

BACKGROUND OF THE INVENTION

1. Field of the Invention

This invention relates to a purifying apparatus possessing a vapor dispersing device such mechanism as to deflect a current of vapor to a specific direction or a purifying apparatus composed of a distillation column and a re-boiler. More particularly, the invention relates to a distillation column and a purifying apparatus which provide distillation and purification of an easily polymerizable compound.

2. Description of Related Art

Distillation is a process which is adopted predominantly for purifying a volatile substance. When the vapor abounding in a low boiling component and ascending to the top of a distillation column is cooled and condensed and the resultant condensate is made to descend from the top of the column and contact the vapor rising from below, the low boiling component in the condensate is gasified and, at the same time, the high boiling component in the vapor is aggregated and liquefied. Consequently, the low boiling component of the vapor departing from the top of the column gains in purity and the high boiling component of the liquid falling to the bottom of the column likewise gains in purity. This refluxing operation constitutes the rectification. Generally, it is in a distillation column that this rectification is carried out.

In this distillation column, the gas-liquid contact for the rectification is implemented by means of trays and a packing disposed in the column. Generally, the liquid supplied from the upper part of the column and the vapor supplied from the lower part of the column are brought into the gas-liquid contact in a cruciform flow or counter flow on the trays and on the surface of the packing eventually to effect gas-liquid mass transfer. It is known that in the gas-liquid mass transfer operation proceeding in the distillation column, the product of this operation is deteriorated by the inferiority of the gas-liquid contact and the inclusion of the bottom liquid of the distillation column in the product. When the compound for distillation happens to be an easily polymerizable compound, the formation of a polymer degrades the efficiency of separation and purification and deteriorates the quality of the product of distillation and the polymer itself adheres to the apparatus and blocks the flow paths for the vapor and the liquid possibly to the extent of obstructing continuous operation of the apparatus.

When the gas phase introduced into the distillation column is drifted only in a limited part, for example, the gas-liquid contact is not sufficiently effected and the efficiency of separation and purification is degraded. Particularly, when the easily polymerizable compound is distilled, it forms a polymer and the polymer adheres to and clogs the various devices used in the process of purification, with the result that the efficiency of separation and purification will be degraded and the quality of the product will be deteriorated. The process, therefore, demands early removal of the polymer. The removal of this polymer compels the process of purification to stop and the removal of adhering polymer is generally difficult.

The degradation of the efficiency of separation and purification and the polymerization mentioned above are readily caused by the drift which is generated in the bottom part of the distillation column. The distillation column generally incorporates therein a re-boiler for gasifying part of the bottom liquid of the column and a re-boiler vapor inlet part for forwarding the produced vapor into the interior of the column for the purpose of heating the bottom of the column. When the vapor blown out of this re-boiler is immediately supplied from the lateral side of the column without being rectified via the nozzle of the inlet part, the vapor in the distillation column is drifted only in part of the cross section of the column by virtue of the propelling force thereof tending upward. Further, in consequence of the upward drift, the liquid flowing down from the upper part of the distillation column is likewise drifted and the gas-liquid contact is rendered deficient. As a result, the efficiency of separation in the distillation column is lowered and the yield of product is degraded. Further, the drift of the vapor gives rise to a vapor stagnating part inside the distillation column and the condensation of the easily polymerizable compound in the gas phase induces the compound to form a polymer easily.

From the re-boiler, the bottom liquid of the column circulated via the re-boiler is copiously blown in besides the vapor. As this vapor ascends at the prevalent speed inside the distillation column, it entrains splashed droplets and the liquid containing the bottom liquid of the column is carried to the trays in the upper stages together with the vapor. To be specific, the efficiency of separation by distillation is degraded because the vapor flowing to the upper part of the distillation column entrains the splashed droplets of the bottom liquid of the column and part of the bottom liquid of the column is suffered to mingle into the product of distillation at the top of the column.

Particularly where the object of distillation is such an easily polymerizable compound as acrylic acid or a product of the esterification thereof, the polymerization due to the drift tends to occur easily. Acrylic acid, for example, is produced by catalytic gas phase oxidation of propylene and/or acrolein with a molecular oxygen-containing gas. The acrylic acid-containing liquid consequently formed is distilled in the distillation column. Since this acrylic acid-containing liquid has a composition containing such impurities as water, acetic acid, and acrolein, the polymerization of acrylic acid occurs very easily. The polymerization of (meth)acrylic acid, therefore, is repressed by adding various polymerization initiators such as hydroquinone, methoquinone, and phenothiazine either singly or in the form of a mixture of two or more members to the process of production. When the vapor containing acrylic acid is led from the re-boiler to the distillation column, however, since the polymerization inhibitor exists only in the liquid phase, the vapor or the condensed liquid from the gas phase part contains substantially no polymerization inhibitor and, on being heated, easily undergoes polymerization. Particularly, the condensation in the gas phase part tends to occur in the vapor stagnating part which is generated by the drift of vapor inside the column and, as a result, induces polymerization in the column.

As a method for preventing the splashed droplets from being entrained by the vapor in the distillation column, JP-A-03-196,801 discloses an invention which, in an operation for flash distillation, aims to accomplish this prevention by providing the distillation column at the center thereof with an umbrella baffle plate separated from the inner wall of the distillation column. JP-A-51-2,675 likewise discloses a method for preventing a quenching column from clogging a nozzle led to the center of the quenching column by depriving the quenching column of a plate for collision and dispersion of gas and causing the nozzle to extend obliquely downward in the direction of the central part of the bottom liquid surface of the column and eventually join the interior of the column instead of thrusting through the wall of the column. The polymerization, therefore, is prevented by excluding the plate for collision and dispersion of gas thereby limiting the portion giving rise to a temperature gradient from the temperature of the quenching gas to the temperature of the condensed liquid only to the part of the wall of the column that surrounds the base of the nozzle. This invention has originated in the light of the fact that when the vapor spouted through a gas blowing nozzle thrust to the center of a quenching column is a polymerizing unsaturated compound and the neighborhood of the nozzle is not suddenly cooled fully satisfactorily, a high boiling substance adheres to the inner wall of the nozzle, gains in growth, and clogs the nozzle again and again.

Unfortunately, the method disclosed in JP-A-51-2,675 mentioned above suffers the condensation of vapor phase substances by contacting with the nozzle, though it is inherently capable of preventing the nozzle from being clogged. Further, by merely discharging the reaction gas via the nozzle in the direction of the bottom liquid in the column, the splashed droplets cannot be prevented from being entrained by the vapor fully satisfactorily and the efficiency of separation and purification cannot be exalted fully satisfactorily.

SUMMARY OF THE INVENTION

This invention aims to prevent the vapor from drifting in the distillation column, improve the efficiency of distillation, and prevent the vapor from undergoing polymerization as well. It also aims to inhibit the bottom liquid of the column from entraining splashed droplets and improve the efficiency of distillation.

The inventors, after pursuing a study on distillation columns, have discovered that, by disposing a vapor dispersing apparatus furnished with an opening part of a specific area directed downward from the horizontal direction at the vapor inlet part of a re-boiler, the drift of the vapor from the re-boiler is repressed, the efficiency of separation in the distillation column is improved, and the polymerization of the vapor inside the column is inhibited. This invention has been perfected as a result.

The problems enumerated above are accomplished by the following items (1)–(10).

(1) A purifying apparatus characterized by being equipped with a vapor dispersing device positioned in a vapor inlet part of the apparatus on the lateral inside thereof an opening part facing downward from the horizontal direction and a horizontal projected cross section area in the range of 10–40% of the cross section area of the apparatus.

(2) A purifying apparatus according to the item (1) mentioned above, wherein the distance from the opening part of the vapor dispersing device to the liquid level in the bottom part is in the range of 0.1–5 times the diameter of the vapor inlet part.

(3) A purifying apparatus according to the item (1) mentioned above, wherein the purifying apparatus is a plate tower or a packed tower and the distance from the opening part of the vapor dispersing device to the lowermost tray or a packing supporting member is in the range of 1.5–8 times the diameter of the vapor inlet part.

(4) A purifying apparatus according to the item (1) mentioned above, wherein the apparatus is provided with not less than two vapor dispersing devices or the vapor dispersing device is provided with not less than two opening parts.

(5) A purifying apparatus according to the item (1) mentioned above, wherein the vapor dispersing device is provided in the upper part thereof with a hole for releasing a vapor and the total hole area is in the range of 0.001–2% of the cross section area of the apparatus.

(6) A purifying apparatus possessed of a distillation column and a re-boiler disposed outside the column, characterized by being equipped with a vapor outlet nozzle of the re-boiler connected to the column side wall in the gas phase part of the bottom of the distillation column and a vapor dispersing device positioned in a vapor inlet part owned by the apparatus on the lateral inside thereof an opening part facing downward from the horizontal direction and a horizontal projected cross section area in the range of 10–40% of the cross section area of said apparatus.

(7) A purifying apparatus according to the item (6) mentioned above, wherein the distillation column is a purifying apparatus set forth in any of the items (2)–(5) mentioned above and equipped with a molecular oxygen supplying part.

(8) A distillation column according to any of the items (1)–(5) mentioned above, characterized by being used for distilling an easily polymerizable compound.

(9) A distillation column according to the item (8) mentioned above, wherein the easily polymerizable compound is (meth)acrylic acid and/or an ester thereof.

(10) A distillation column, characterized by being equipped on the inner wall of a distillation column with a mechanism for deflecting the re-boiler vapor introduced into the distillation column downward from the horizontal direction.

The installation of the vapor dispersing device in the re-boiler vapor outlet results in endowing the distillation column with improved efficiency of separation because the device is capable of repressing the drift of the vapor in the column and affording fully satisfactory gas-liquid contact.

This installation also brings about such effects as curbing the drift of the vapor in the column, decreasing the vapor stagnating part in the column, and allaying the condensation of the vapor and thereby inhibiting the occurrence of a polymer.

The formation of polymer may be further repressed by providing the distillation column or the purifying apparatus with a molecular oxygen supplying part.

DESCRIPTION OF PREFERRED EMBODIMENT

This invention concerns a distillation column equipped in the interior thereof with a vapor dispersing device of a specific structure. Generally, the distillation column which is used for purifying by distillation an easily polymerizable compound is provided, with the object of recirculating a substance aimed at and improving the efficiency of distillation and separation, with a re-boiler for vaporizing the bottom liquid of the column. When the re-boiler vapor is supplied in an unrectified state into the distillation column, however, the gas-liquid contact is prevented from proceeding sufficiently and the efficiency of separation in the column is degraded because the upward propelling force resulting from heating the interior of the distillation column generates the drift of the re-boiler vapor only in part of the cross section of the column. The distillation column of this invention is enabled to spout the re-boiler vapor downward from the horizontal direction and prevent the vapor from drifting upward because it is provided inside the bottom thereof with a vapor dispersing device of a specific structure. It is additionally enabled by this device to prevent the liquid descending the interior of the distillation column from forming a drift. As a result, the dispersion of the vapor can be uniform and the gas-liquid contact can be attained fully satisfactorily.

The re-boiler vapor contains the bottom liquid component of the column which is circulating via the re-boiler. Since the re-boiler vapor is enable to be spouted downward from the horizontal direction, the liquid can be prevented from entraining splashed droplets and the bottom liquid component of the column can be prevented from mingling into the product.

Further, by setting the distance from the opening part in the vapor dispersing device to the liquid level in the bottom of the column and the distance from the opening part in the vapor dispersing device to the lowermost tray (3) and to the packing supporting member within respectively specified ranges, it is made possible to adjust the retention time, further inhibit the polymerization, prevent the product from degradation of quality, and improve the efficiency of distillation and separation.

Incidentally, the term "purification" as used in this invention shall be interpreted as comprising any one of a process of distillation, stripping and absorption. The term "distillation" herein refers to the operation of separating a gas-liquid mixture into the components by utilizing the differences in the vapor pressures of the components. Then, the term "stripping" herein refers to the operation of expelling from a solution one or more components present therein by causing this solution to contact a gas not containing the components. Further, the term "absorption" herein refers to the operation of causing one or more components in a gas mixture to be absorbed in a solvent. The term "distillation as used herein shall be interpreted as embracing rectification. Now, this invention will be described in detail below.

(1) Distillation column

As the purifying apparatus to be used in this invention, all the contrivances such as, for example, a distillation column, a stripping column, and an absorption column itself which are used in the general steps of distillation and purification are included. When the object for distillation is an easily polymerizable compound, particularly when acrylic acid is produced by the method of catalytic gas phase oxidation of propylene and/or acrolein, for example, various kinds of distillation columns adapted to alter distillation temperature, pressure, etc. with the object of cooling and washing in counter flow the acrylic acid-containing gas obtained by the catalytic gas phase oxidation with a solvent and recovering the acrylic acid from the collected mixture of the solvent with the acrylic acid are included. Further, such contrivances as a solvent separating column, an azeotropic separating column, an acetic acid separating column, and a high boiling substance separating column which are intended to effect distillation, purification, and separation are included in the category of the purifying apparatus contemplated by this invention in spite of their designations.

The distillation column which constitutes itself the purifying apparatus is available in various types such as a plate tower, a packed tower, a wet wall tower, and a spray tower. This invention prefers the plate tower or the packed tower to the other types mentioned above. The reason for this preference is that the tower excels in the efficiency of gas-liquid contact and in the efficiency of distillation and separation. The mode of the contact to be established between the relevant fluids may be selected from among cruciform flow, counter flow, parallel flow, and perfect mixture, for example. The reason for the arbitrariness of this mode of contact between the relevant fluids is that this invention aims to inhibit the otherwise possible polymerization of the substance under treatment and enhance the efficiency of distillation and separation by adjusting the flow of the vapor from the re-boiler within the purifying apparatus.

(2) Re-boiler

The purifying apparatus of this invention may not be provided with the re-boiler (20). As shown FIG. 1A, it may have the distillation column (10) mentioned above provided with the re-boiler (20). When the purifying apparatus is possessed of the distillation column (10) and the re-boiler (20) disposed outside the distillation column (10), therefore, the re-boiler (20) which can be effectively used therein is the so-called heat exchanger without reference to the designation employed therefor. It has only to be capable of enabling the liquid condensed in the apparatus to be heated and vaporized again. As concrete examples of the heat exchanger, a shell and tube cylindrical heat exchanger, a floating head heat exchanger, a U-shaped tube heat exchanger, a fixed tube sheet heat exchanger, a double pipe heat exchanger, a single pipe heat exchanger, and a plate heat exchanger may be cited. Even when the purifying apparatus is possessed of the re-boiler (20), it is necessary that the re-boiler (20) should be disposed outside the distillation column (10). The reason for this external disposition is that when the re-boiler (20) belongs to a type for insertion in the column, the presence of this re-boiler (20) itself compels the vapor to generate a drift or renders adjustment of the drift of the vapor difficult.

(3) Purifying apparatus

As the purifying apparatus of this invention, a distillation column, a stripping column, or an absorption column may be used either alone or in coordination with a re-boiler. As shown FIG. 1A, when the distillation device incorporates therein a re-boiler (20), it is necessary that the re-boiler (20) should be disposed outside the distillation column (10) instead of being directly connected to the column and the vapor outlet nozzle (2) of the re-boiler (20) should be connected to the lateral wall of the column (10) in the gas phase part (7) of the bottom of the distillation column (10). In this case, the nozzle (2) is preferred to be joined to the distillation column (10) perpendicularly to the distillation column (10) so that the vapor may be introduced in the horizontal direction into the distillation column (10) which is installed upright. The reason for the perpendicular joint is that when the nozzle (2) is connected at an acute angle to the distillation column (10), the vapor introduced into the distillation column (10) flows up or down the interior of the distillation column (10) and, consequently, the vapor of this behavior is not dispersed but is suffered to stagnate within the vapor dispersing device to be used in the present invention. In consideration of the thermal efficiency, the vapor outlet nozzle (2) is preferred to be connected to the shell of the bottom of the distillation column (10) over the shortest possible distance.

The size of the distillation column (10) and that of the re-boiler (20) purifying apparatus mentioned above may be properly selected to suit the physical properties of the easily polymerizing substance, the quantity of purification, the purpose of purification etc. When the purifying apparatus of this invention happens to be a distillation column (10) or to incorporate therein a distillation column (10), therefore, the distillation column (10) of the size fit for use herein has a diameter has a diameter in the range of 300 mm–10000 mm, for example. In this case, the inlet diameter of the re-boiler (20) is properly 0.1–0.9 times, preferably 0.15–0.7 times, and more preferably 0.2–0.5 times, the diameter of the column. The flow volume of the vapor to be introduced into the purifying apparatus may be properly selected, depending on the inlet diameter of the re-boiler (20), the vapor pressure of the easily polymerizing substance, etc. The flow volume fit for use herein may be in the range of 500–1,500,000 $m^3/hr$, preferably in the range of 1,000–1,000,000 $m^3/hr$.

(4) Vapor dispersing device

The vapor dispersing device (1) to be used in this invention is disposed in the distillation column (10). It requires to possess a vapor opening part (6) such that the vapor is spouted from the re-boiler nozzle downward from the horizontal direction and that the opening part (6) mentioned above has a horizontal projected cross section area in the range of 10–40% of the cross section area of the column. In other words, the distillation column (10) requires to possess on the inner wall thereof a mechanism for deflecting the vapor downward from the horizontal direction. This vapor dispersing device (1) has only to be so disposed as to have part thereof held in contact with the inner wall of the column. It may be disposed directly on the leading terminal part of the re-boiler vapor outlet nozzle (2) which penetrates into the distillation column (10) from outside. The shape of the vapor dispersing device (1) does not need to be particularly defined but is only required to satisfy the following conditions.

In this invention, the opening part (6) of the vapor dispersing device (1) may be disposed above the vapor inlet part of the re-boiler nozzle (2) in such a manner as to encircle part of the inlet part. The leading terminal of the re-boiler nozzle (2) may be so designed as to penetrate through the lateral wall of the gas phase part (7) of the distillation column (10) into the interior of the distillation column (10) and the part of the re-boiler nozzle (2) thrust into the distillation column (10) may be utilized as the vapor dispersing device (1) contemplated by this invention. The reason for requiring the vapor dispersing device (1) to possess an opening part (6) facing down from the horizontal direction is that the vapor from the re-boiler (20) is allowed to flow provisionally down the interior of the distillation column (10) by causing the vapor from the nozzle (2) to spout in the downward direction. Consequently, the vapor earns an addition to the distance of its ascent because it starts ascending the interior of the distillation column (10) again after passing through the opening part (6). Further, since the linear velocity of the vapor during this repeated ascent is decreased to the speed corresponding to the cross section of the column (10), the vapor ascending the lower part of the distillation column (10) is allowed an ample time for attaining uniform dispersion throughout the cross section of the column (10). As a result, the possible gas-liquid drift near the bottom of the column (10) is repressed, the gas-liquid contact is permitted to proceed fully satisfactorily, and the efficiency of separation is enhanced.

The vapor dispersing device (1) to be used in this invention is preferred to have at least part thereof connected to the inner wall of the distillation column (10). The reason for requiring at least part of the apparatus to be so connected is that while the re-boiler vapor entering the distillation column (10) via the vapor inlet formed in the inner wall of the column immediately would move up the interior of the distillation column (10) owing to the prevalent temperature in the column, the connection of the vapor dispersing device in the manner mentioned above to the inner wall of the distillation column (10) is capable of guiding most of the vapor down the interior of the distillation column (10) and inducing dispersion of the vapor as well.

Generally, the vapor departing from the re-boiler (20) via the vapor outlet thereof entrains the splashed particles of the bottom liquid of the column which abound in high boiling substances because the vapor itself as well as the bottom liquid of the column (10) being circulated on the bottom of the column via the re-boiler (20) is blown in through the vapor outlet of the re-boiler (20). When the vapor dispersing device (1) possessing an opening part (6) facing downward from the horizontal direction is disposed in the vapor outlet of the re-boiler (20), therefore, the splashed droplets are separated from the vapor because they have larger inertial force than the vapor and, therefore, are allowed to depart from the stream of the vapor and collide against the wall of the vapor dispersing device (1). As a result, the vapor is prevented from entraining the splashed droplets of the bottom liquid of the column and the efficiency of distillation is improved.

For the purpose of preventing the vapor from forming a drift and from entraining the splashed droplets of the bottom liquid of the column, the cross section of the opening of the vapor dispersing device (1) is defined in the range of 10%–40% of the cross section of the column. With the object of obtaining uniform dispersion of the vapor in the column (10), it is necessary that the vapor dispersing device (1) should be prevented from blocking the cross section of the column and the horizontal projected cross section of the vapor dispersing device (1) (cross section of the opening) should be decreased to the fullest possible extent. This cross section area is preferred not to exceed the upper limit, 40%, mentioned above. When the vapor dispersing device (1) is disposed in the manner described above and the vapor is consequently blown in toward the lower part of the column, namely the surface of the bottom liquid of the column, the possibility ensues that the bottom liquid of the column copiously containing high boiling substances will be flung up from the surface of the liquid by the kinetic energy of the vapor and consequently suffered to entrain the splashed droplets of the liquid. It is, therefore, necessary that the cross section area of the opening part (6) of the vapor dispersing device (1) should be enlarged enough to decrease the kinetic energy. The cross section area, therefore, is preferred not to be smaller than the lower limit, 10%.

The size of the opening part in the vapor dispersing device (1) to be used in this invention does not need to be fixed but may be varied within the range mentioned above by means of a mechanism specifically adapted to effect such variation. When the distillation column (10) or the purifying device contemplated by this invention is put to use, the area of the opening part may be varied as synchronized with variations in the kind of compound for distillation, the amount of the vapor spouted from the re-boiler (20), the internal pressure and temperature of the distillation column (10), etc.

Figures 5A, 5B:
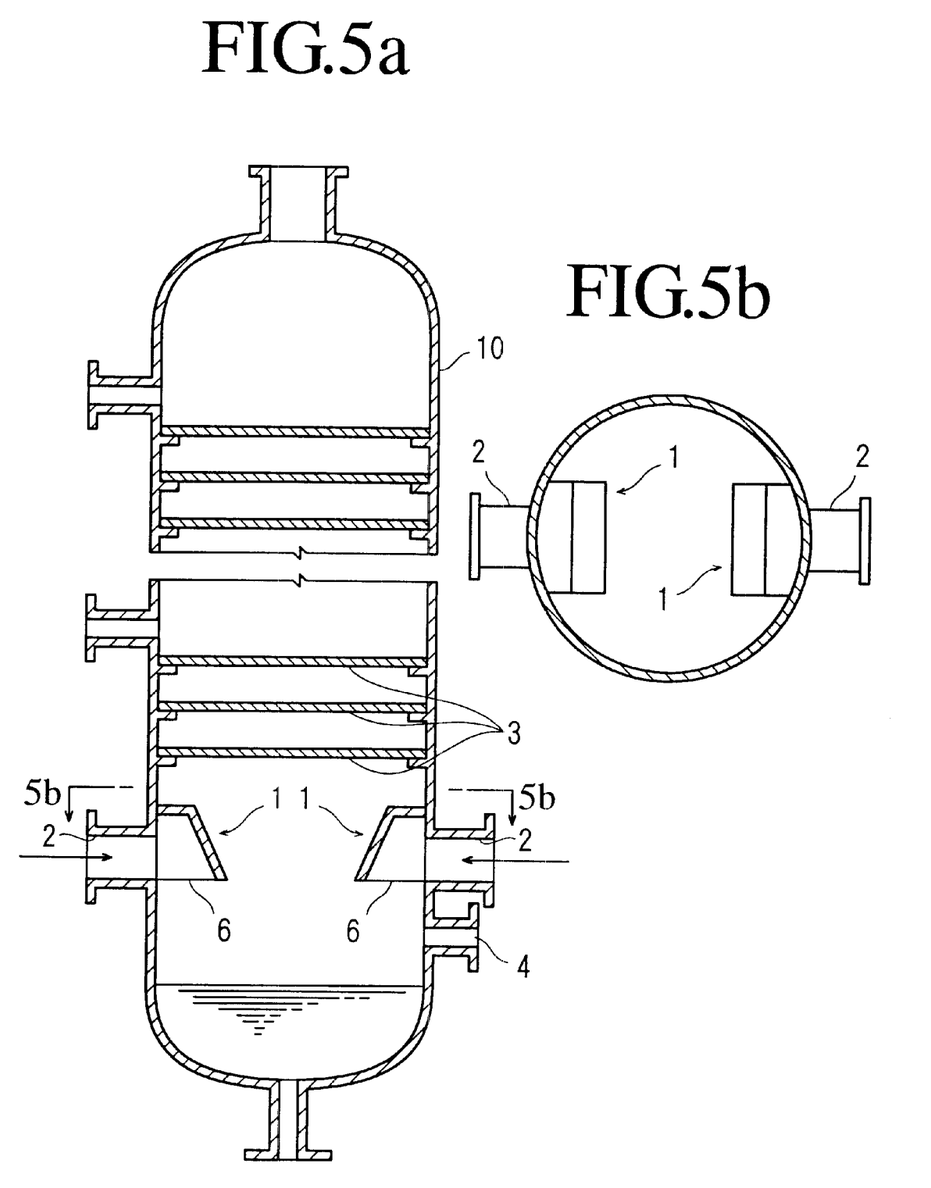
FIG. 5A is a cross section diagram illustrating a plate tower type distillation column (10) having two re-boiler vapor nozzles connected thereto and two vapor dispersing devices (1) disposed therein.
FIG. 5B is sectional view taken substantially along line 5b–5b of FIG. 5A.
Figures 6A, 6B:
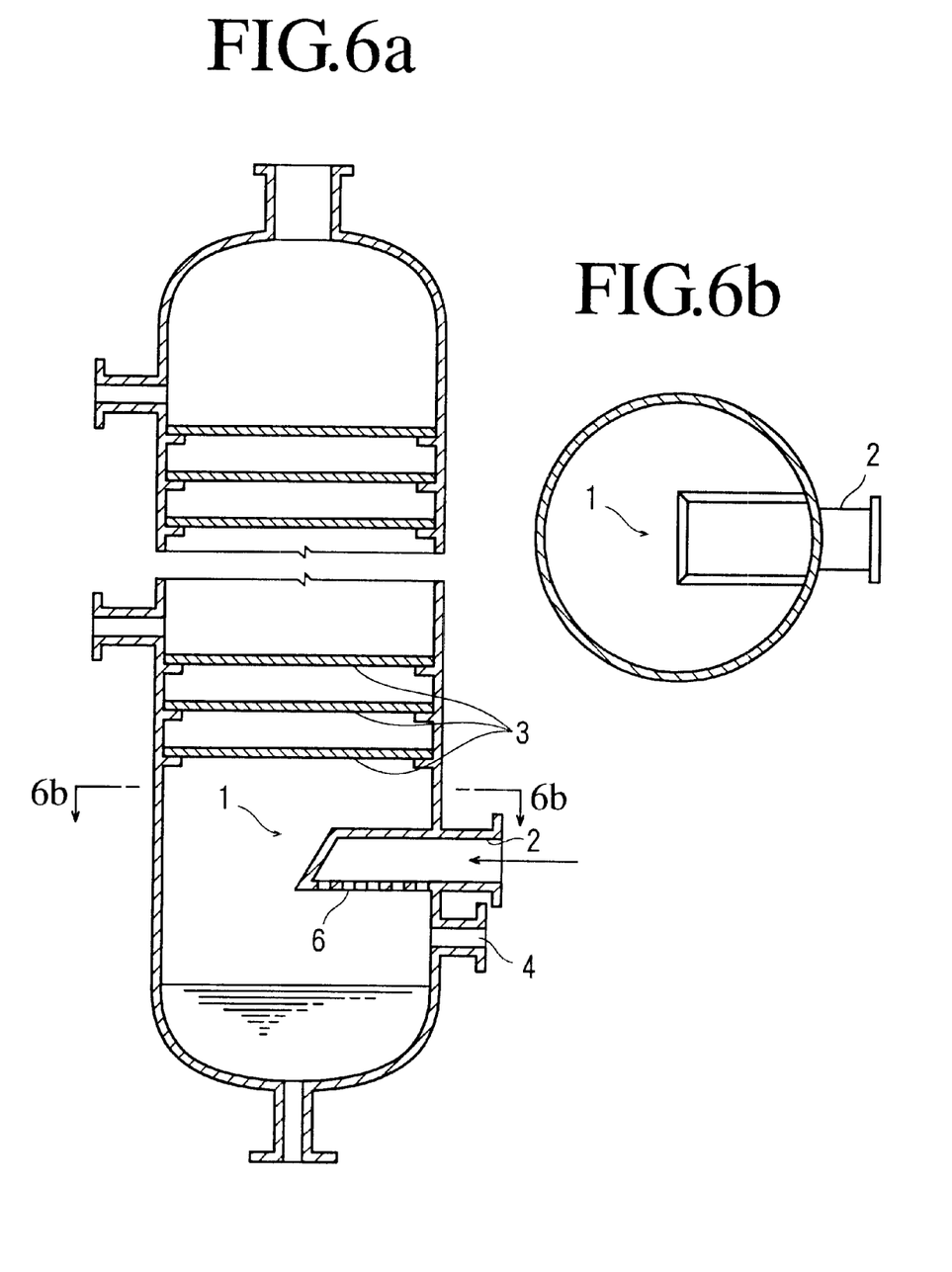
FIG. 6A is a cross section diagram illustrating a plate tower type distillation column (10) provided with a vapor dispersing device (1) possessed of a plurality of vapor opening parts (6).
FIG. 6B is sectional view taken substantially along line 6b–6b of FIG. 6A.

The number of vapor dispersing devices (1) or the number of opening parts (6) to be formed in the vapor dispersing device (1) does not need to be limited to one as shown FIG. 5A and FIG. 6A. This invention allows use of a plurality of such devices (1) or opening parts (6). The uniformity of the vapor in the column is exalted in proportion as the number of points of introduction is increased. When the purifying apparatus uses two or more re-boilers (20) and two or more re-boiler vapor outlet nozzles (2) as well as when the apparatus is furnished with two or more vapor dispersing devices (1) or the vapor dispersing device (1) is furnished with two or more opening parts, the total of the cross sections area of the opening parts is set in the range mentioned above. Incidentally, the shape of the opening part in the vapor dispersing device (1) does not need to be particularly defined but is only required to have a horizontal projected cross section area in the range mentioned above. Various shapes such as, for example, square, circle, and ellipse are available for the opening part.

Figures 1A, 1B:
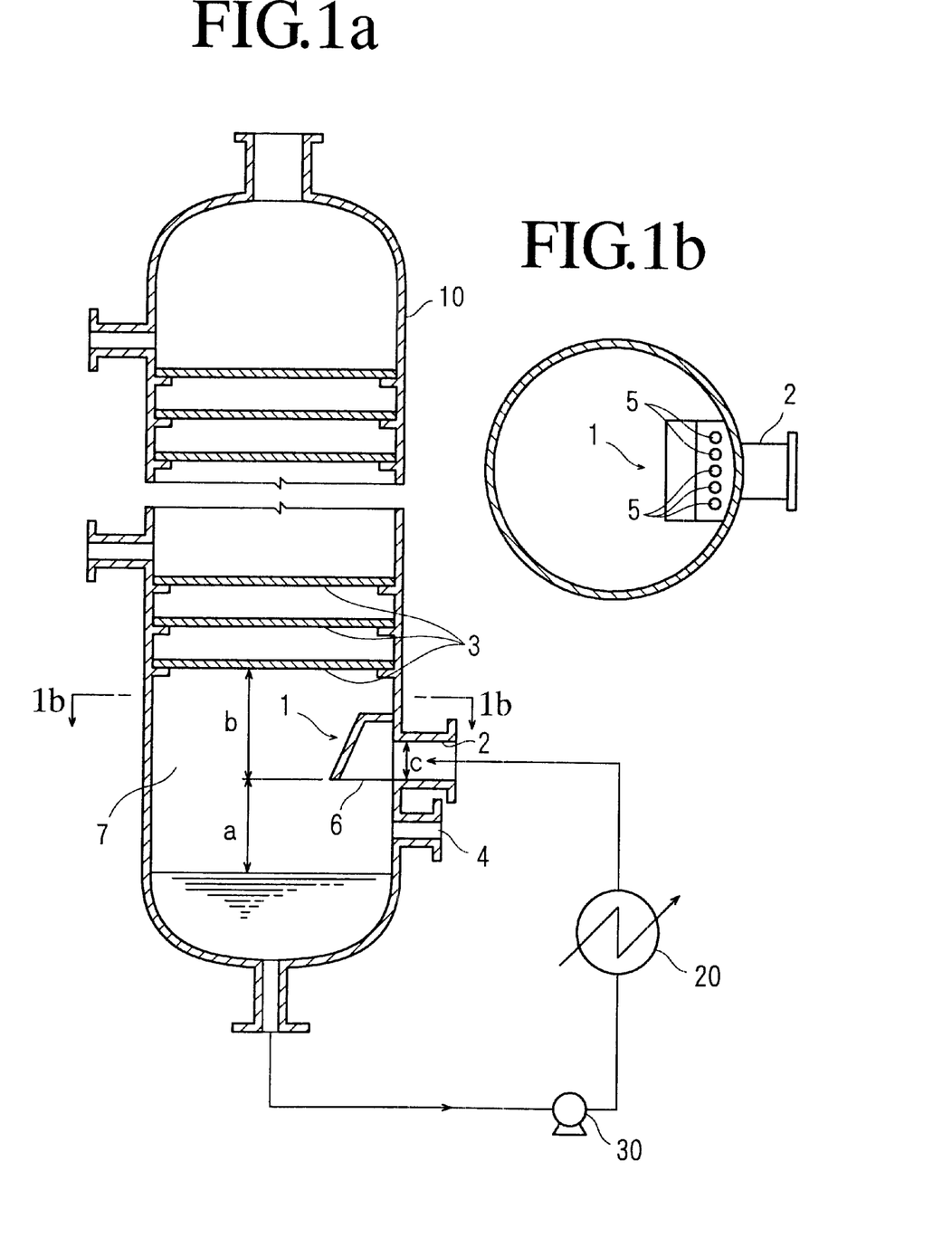
FIG. 1A is a cross section illustrating a plate tower type distillation column (10) equipped with a rectangular vapor dispersing device (1), a re-boiler (20) and a pump (30).
FIG. 1B is sectional view taken substantially along line 1b–1b of FIG. 1A.

As shown FIG. 1A, this invention enjoys a further addition to the effect thereof by defining the distance (b) between the opening part (6) of the vapor dispersing device (1) and the lowermost tray (3)or the rectifying mechanism such as of the packing supporting member as a length of not less than 1.5 times the diameter (c) of the vapor inlet of the re-boiler (20) for the purpose of attaining uniform dispersion of the vapor in the column (10). If this distance is less than 1.5 times the diameter (c), the vapor will not be satisfactorily prevented from entraining the splashed droplets. If the distance (b) is unduly large, the unnecessary gas phase part (7) will enlarge and the retention time will increase possibly to the extent of suffering the vapor in the column (10) to condense and polymerize. It is, therefore, necessary that the distance (b) should be defined by an upper limit of 8 times the diameter (c). For this reason, it is necessary that the distance (b) from the opening part (6) of the vapor dispersing device (1) to the lowermost tray (3) or the packing supporting member as a length in the range of 1.5–8 times, preferably 2–5 times, the diameter (c) of the vapor outlet nozzle (2) of the re-boiler (20).

When the distance (a) from the opening part (6) of the vapor dispersing device (1) to the surface of the liquid in the lower part of the column is simultaneously defined as a length of not less than 0.1 times the diameter (c) of the vapor outlet nozzle (2) of the re-boiler (20), the distance (a) proves effective in repressing the possible hurl of the splashed droplets from the bottom liquid of the column and yet results inevitably in enlarging the unnecessary gas phase part (7). Thus, this distance (a) is preferred to be in the range of 0.1–5 times, preferably 0.5–2 times, the nozzle diameter (c). Such sizes as the diameter of the distillation column as a component member of the purifying apparatus and the diameter of the inlet of the re-boiler may be properly selected as described above. Further, the flow volume of the vapor may be likewise selected properly, depending as on the vapor pressure of the easily polymerizing substance. This invention accomplishes the object thereof effectively by adjusting such dimensions within the relevant ranges mentioned above.

The vapor dispersing device (1), as illustrated in FIG. 1B, may be further provided in the upper part thereof with holes (5) for releasing a vapor. Properly, the total area of these holes (5) is in the range of 0.001–2%, preferably 0.005–1%, of the cross section area of the apparatus. The reason for the existence of the holes (5) having a area in the range mentioned above is that this hole (5) accomplishes the purpose of repressing the stagnation of the vapor in the vapor dispersing device (1) and, at the same time, the purpose of dispersing the vapor effectively in the empty space directly above the vapor dispersing device (1).

The shape of the vapor dispersing device (1) to be used in this invention will be described with the aid of diagrams. The portions "A" respectively of FIGS. 1A–8A illustrate varying vapor dispersing devices (1) as viewed of cross section of the column and the portions "B" thereof illustrate these devices as viewed from the line b—b of the column of FIG. A.

Figures 2A, 2B:
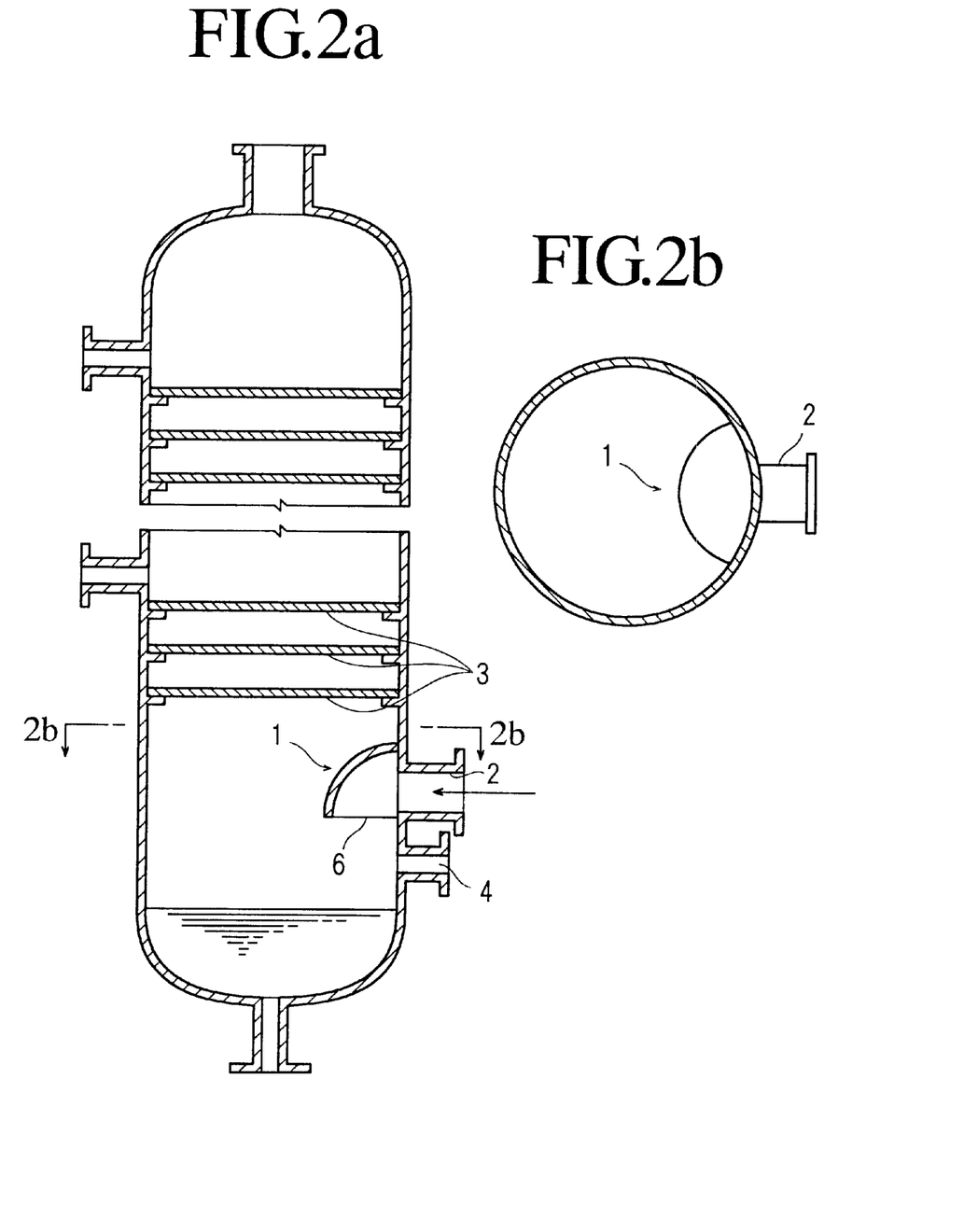
FIG. 2A is a cross section diagram illustrating a plate tower type distillation column (10) provided with a circular vapor dispersing device (1).
FIG. 2B is sectional view taken substantially along line 2b–2b of FIG. 2A.
Figure 4A:
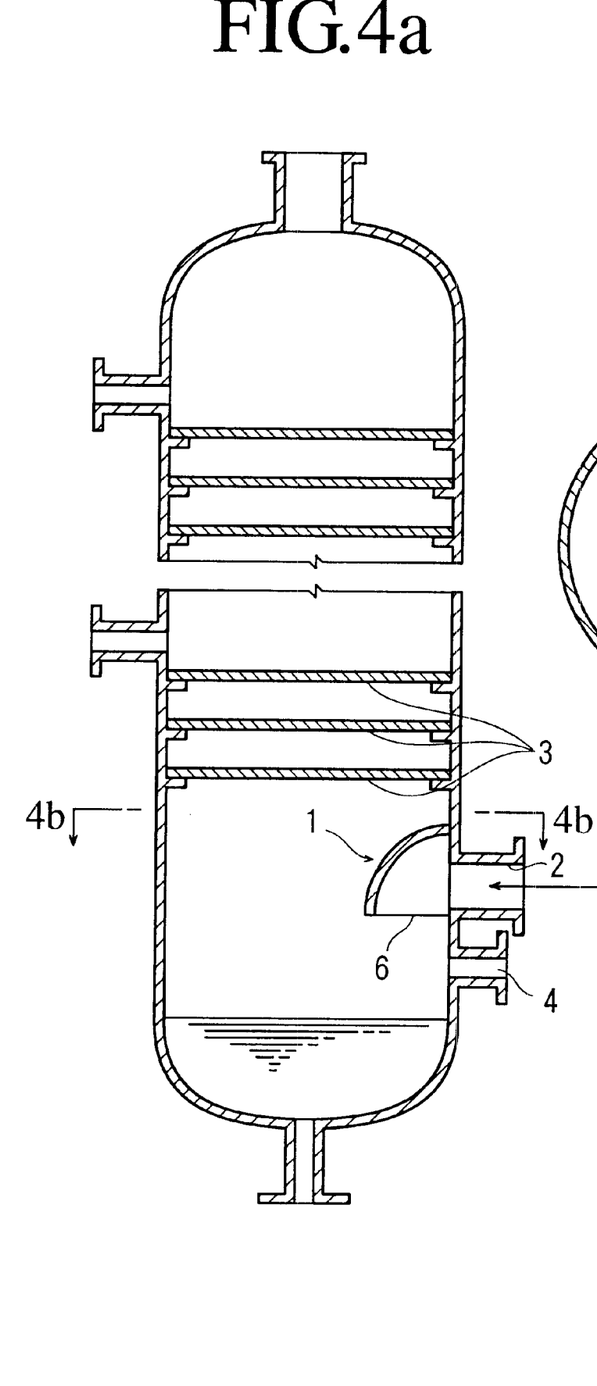
FIG. 4A is a cross section diagram illustrating a plate tower type distillation column (10) provided with a triangular vapor dispersing device (1).

In this invention, the vapor dispersing device (1) is preferred to be disposed in such a manner as to have part thereof connected to the inner wall of the distillation column (10) as illustrated in FIG. 1A. The vapor dispersing device (1) may be constructed by forming the upper part with a flat surface and joining to the flat surface lateral parts extending vertically or diverging downward after the fashion of a fan as illustrated in FIG. 1A or may be constructed by joining a curved member as illustrated in FIG. 2A or a triangular member as illustrated in FIG. 4A respectively to the inner wall. With consideration for the possible stagnation of the substance for distillation, however, the vapor dispersing device (1) is preferred to be in an arc-shaped form which inhibits partial stagnation of the substance being distilled.

Figures 3A, 3B:
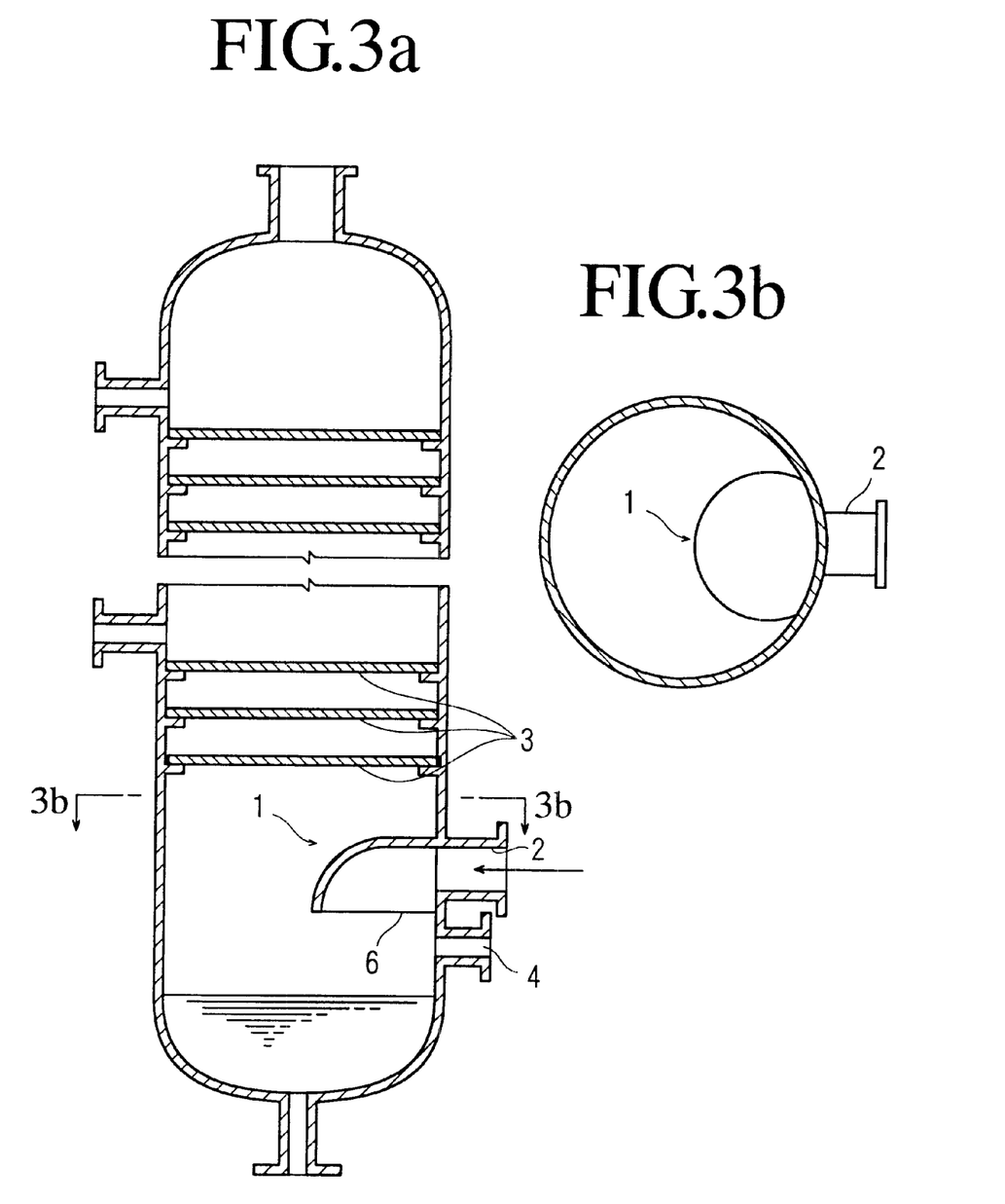
FIG. 3A is a cross section diagram illustrating a plate tower type distillation column (10) provided with a circular vapor dispersing device (1).
FIG. 3B is sectional view taken substantially along line 3b–3b of FIG. 3A.

Even when the projection of the vapor dispersing device (1) from the inner wall of the distillation column (10) is not connected to the vapor inlet part (2) but is formed from above the inlet part (2) as illustrated in FIG. 2A or FIG. 4A, the vapor dispersing device (1) may be disposed so as to be connected to the upper end of the vapor inlet part as illustrated in FIG. 3A. For the sake of repressing the stagnation of the vapor inside the vapor dispersing device (1), however, the vapor dispersing device (1) is preferred to be so disposed as to be connected to the upper end of the vapor inlet part.

The position of the opening part (6) of the vapor dispersing device (1) may be flush with the lower end of the vapor inlet part (2) as illustrated in FIG. 1A, may be extended below from the lower end of the vapor inlet part (2) as illustrated in FIG. 2A, or may be elongated above from the lower end of the vapor inlet part (2) though not illustrated in any diagram. With the object of uniformly dispersing the vapor, however, the vapor opening part (6) is preferred to be flush with the lower end of the vapor inlet part (2) or to be extended downward from the lower end. Incidentally, the opening parts (6) in the vapor dispersing devices (1) illustrated in FIGS. 1A–5A are opened throughout the entire surfaces.

Figure 4B:
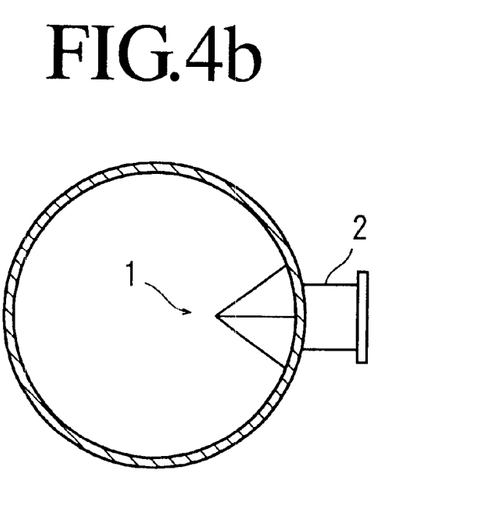
FIG. 4B is sectional view taken substantially along line 4b–4b of FIG. 4A.

The opening part of the vapor dispersing device (1) disposed in the distillation column (10) as viewed from above may be in a rectangular shape as illustrated in FIG. 1B, in an arc-shaped form as illustrated in FIG. 2B or FIG. 3B, in a triangular shape as illustrated in FIG. 4B, or in the shape of a fan or polygon expanded inside the distillation column (10). With the object of facilitating the manufacture of device, the opening part is preferred to be in a rectangular shape. For the sake of repressing the stagnation of the vapor inside the vapor dispersing device (1), the opening part is preferred to be in an arc-shaped form by reason of the scarcity of angular parts. Incidentally, FIG. 1A illustrates one example of the purifying apparatus of this invention which is possessed of a molecular oxygen supply part (4).

Figures 7A, 7B, 7C:
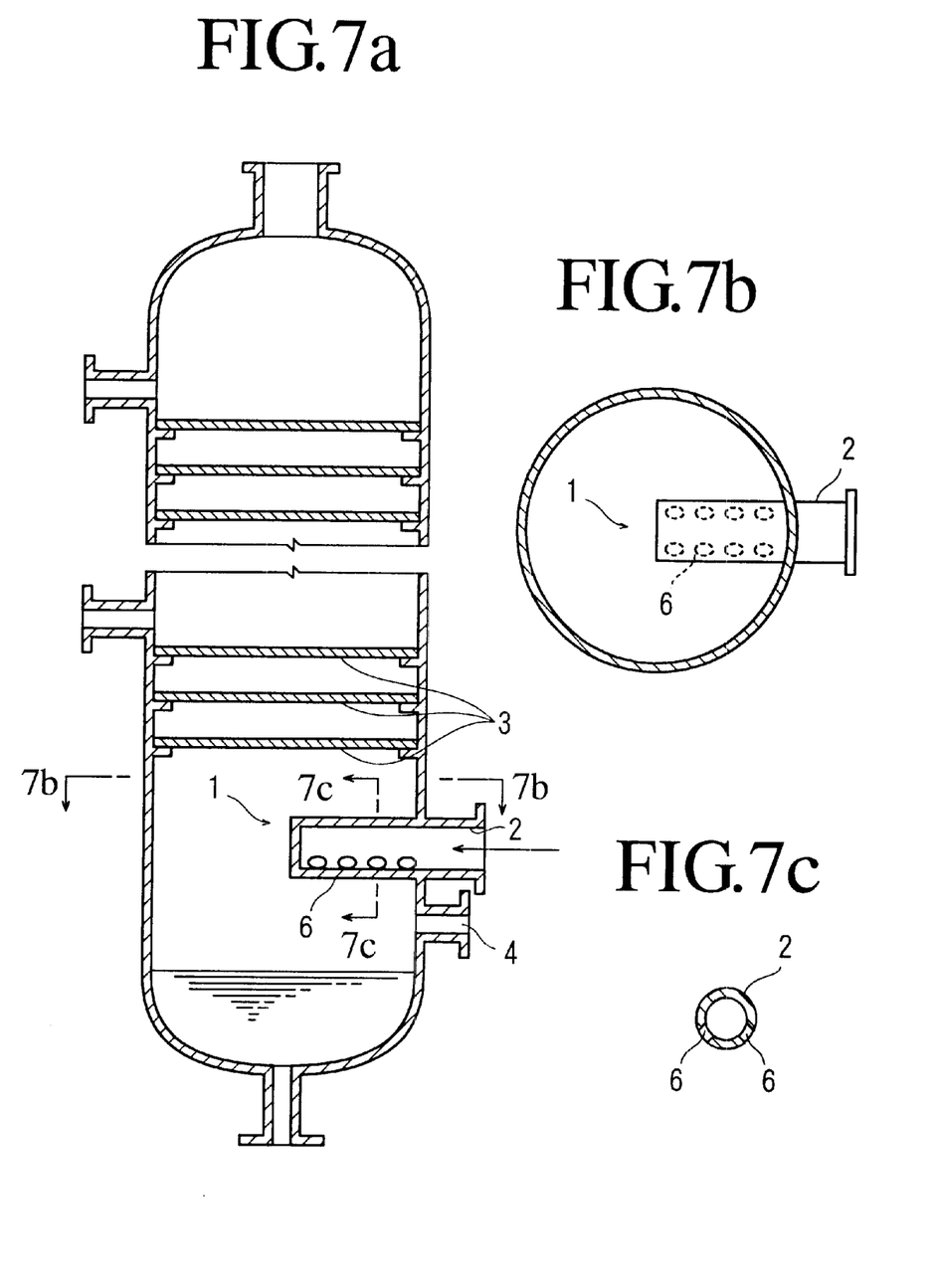
FIG. 7A is a cross section diagram illustrating a plate tower type distillation column (10) equipped with a nozzle type vapor dispersing device (1) having a plurality of hole (5) for releasing a vapor.
FIG. 7B is sectional view taken substantially along line 7b–7b of FIG. 7A.
FIG. 7C is sectional view taken substantially along line c—c of FIG. 7A.
Figures 8A, 8B:
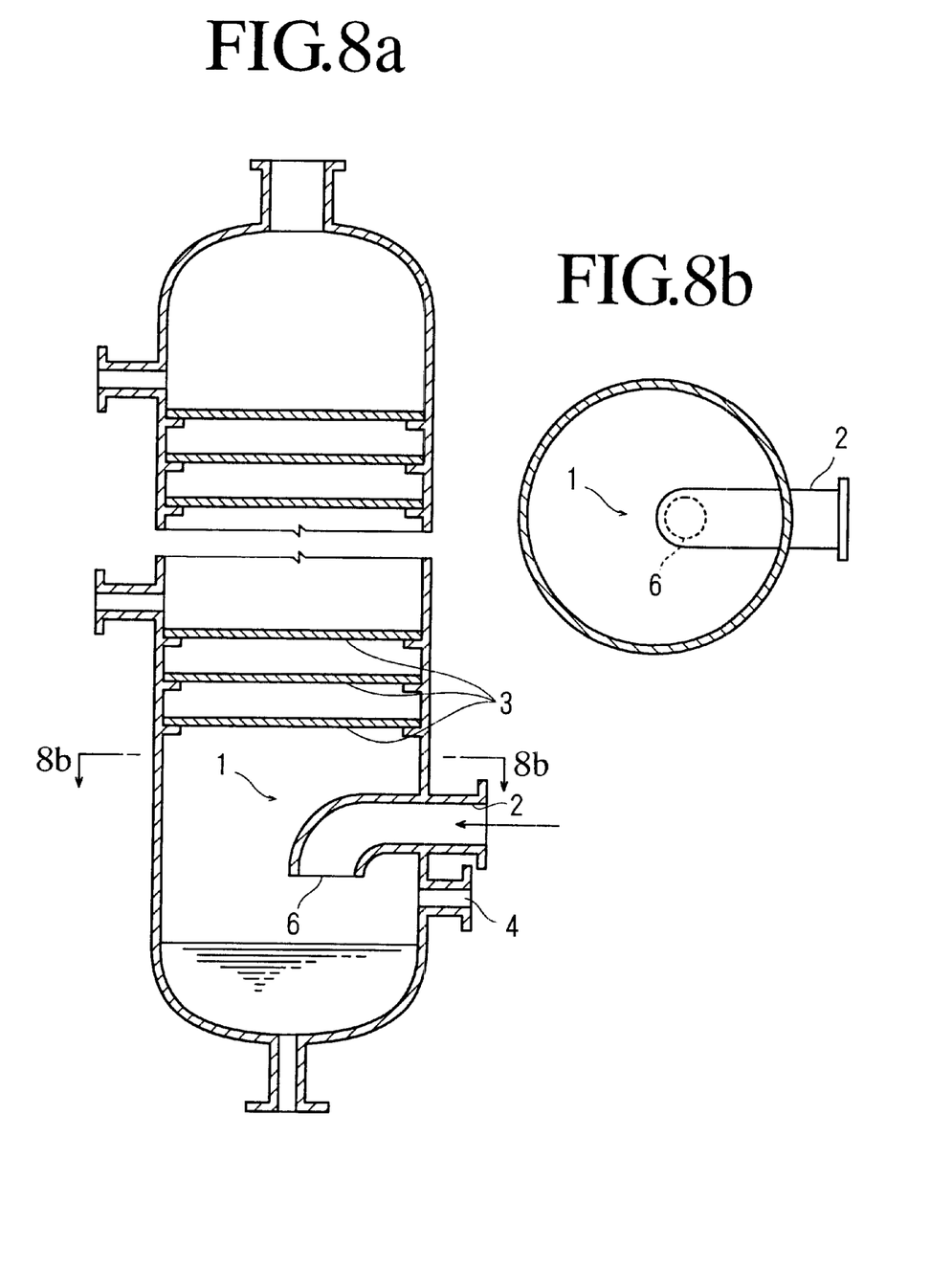
FIG. 8A is a cross section diagram illustrating a plate tower type distillation column (10) provided with a nozzle type vapor dispersing device (1) formed by elongating a re-boiler nozzle (2).
FIG. 8B is sectional view taken substantially along line 8b–8b of FIG. 8A.

The purifying apparatus of this invention may be equipped with a plurality of vapor dispersing devices (1) and, as a natural consequence, furnished with a plurality of re-boiler vapor inlet parts (2) as illustrated in FIG. 5A and FIG. 5B. The reason for this configuration is that the configuration is capable of preventing the vapor from being drifted upward inside the distillation column (10). Optionally, one vapor dispersing device (1) may be furnished with a plurality of opening parts (6) as illustrated in FIG. 6A and FIG. 7A. Then, the vapor dispersing device (1) may have the upper part thereof formed as elongated from the part (6) at which the re-boiler nozzle (2) joins the wall of the gas phase part (7) of the distillation column (10) as illustrated in FIG. 6A. Further, the vapor dispersing device (1) may have the outer shell thereof extended in the shape of a nozzle from the part at which the re-boiler nozzle joins the wall of the gas phase part (7) of the distillation column (10) as illustrated in FIG. 7A and FIG. 8A. FIG. 7A and FIG. 7B illustrate the vapor dispersing device (1) of the shape of a nozzle which is equipped in the lower part from the center thereof with a plurality of opening parts (6). The cross-section of the nozzle-shaped vapor dispersing device (1) is illustrated in FIG. 7C. FIG. 8 depicts the vapor dispersing device (1) of the shape of a nozzle, with the opening part (6) thereof opened throughout the entire surface thereof.

(5) Molecular oxygen supplying part

The purifying apparatus of this invention is preferred to be possessed of a molecular oxygen supplying part (4). In the case of using such an easily polymerizable compound as acrylic acid as the object of distillation, for example, the provision of the molecular oxygen supplying part (4) proves advantageous because acrylic acid is stabilized and consequently prevented from polymerization in the coexistence of molecular oxygen with such a polymerization inhibitor as hydroquinone, methoquinone, or phenothiazine. The supplying part (4) for molecular oxygen has only to be a port which communicates with the external part of distillation column (10) mounted partly in the bottom part of the distillation column (10). Through this port, the molecular oxygen from an oxygen cylinder may be supplied. When the distillation is carried out under a reduced pressure, the supply of molecular oxygen into the bottom part of the distillation column (10) is attained spontaneously because the ambient air inherently containing molecular oxygen flows into the site of distillation.

The position to seat the supplying part (4) for molecular oxygen may be selected anywhere on the bottom part of the distillation column (10). Though this position does not need to be particularly limited to the neighborhood of the re-boiler vapor inlet part, this part is preferred to be positioned in the part underlying the re-boiler vapor inlet part. This particular position proves advantageous because it permits intimate mixture of the ascending re-boiler vapor with molecular oxygen and allows efficient prevention of the possible polymerization.

This invention does not need to limit the number of molecular oxygen supplying parts (4) to one but allows dispersed installation of a plurality of such parts.

(6) Easily polymerizable compound

The purifying apparatus of this invention is furnished with the vapor dispersing device (1) and consequently enabled to enhance the efficiency of separation by deflecting and dispersing the vapor. Thus, it can be used generally for all the compounds that can be adopted as objects for distillation. It, however, particularly fits distillation of easily polymerizable compounds. As concrete examples of the easily polymerizable compound, acrylic acid, methacrylic acid, maleic acid, and esters thereof. Particularly, it is effectively applied to acrylic acid, methacrylic acid, and esters thereof. The pertinent acrylic acid-containing liquid may incorporate therein at least one member from the group of various polymerization inhibitors such as, for example, hydroquinone, methoquinone, phenothiazine, copper salts of dibutyl dithiocarbamic acid, p-phenylene diamines, and N-oxyl compounds.

By using the purifying apparatus of this invention for distilling an easily polymerizable compound, it is made possible to enhance the efficiency of separation and purification in consequence of preventing the vapor from being drifted and, at the same time, prevent the polymerization and preclude the adhesion of polymer to the distillation column or the purification apparatus so as to simplify the operation of removing polymer, and further permit continuous operation of the equipment to last for a long time.

EXAMPLES

Now, this invention will be described more specifically below with reference to a working example.

Example 1

In a stainless steel (SUS 316) distillation column equipped in the top part thereof with a distilling tube, having a re-boiler, i.e. a shell-and-tube heat exchanger, connected to the bottom part thereof, and incorporating therein 35 shelves, continuous purification of acrylic acid was carried out by the use of a molecular oxygen supplying part, 25 mm in diameter, located at a position 200 mm above from the lower end of the re-boiler vapor inlet part.

As the feed material, an acrylic acid solution containing 5 wt. % of maleic acid as an impurity component was used. The distillation was performed under the conditions of 35 mmHg of the operating pressure of the distillation column and 67° C. of the column top temperature. As the polymerization inhibitor, a solution obtained by adding to the acrylic acid solution 100 ppm of phenothiazine based on the amount of the vapor of acrylic acid produced by vaporization was introduced into the column via the bottom thereof. Further, molecular oxygen was injected in an amount of 0.4 mol. % based on the amount of the vapor of acrylic acid produced by vaporization.

The re-boiler vapor inlet part had a circular shape, 400 mm in diameter, and was disposed on the inner wall of the distillation column. In the re-boiler vapor inlet part, a vapor dispersing device (cross section ratio 25%) whose upper part overlying the position of 65 mm from the upper end of the vapor inlet part was in a rectangular shape 600 mm in width and 416 mm in length in the direction of the center of the distillation column, whose lateral part measured 465 mm in maximum length downward from the upper part of the vapor dispersing device, whose open part measured 600 mm in width and 400 mm in length, and whose opening part measured 465 mm in maximum length from the upper part to the opening part of the vapor dispersing device to the opening part was installed. The opening part measured 500 mm from the liquid level and 1500 mm from the lowermost tray (3). The vapor dispersing device was provided in the upper part thereof with four holes for releasing a vapor, 12 mm in diameter (total cross sectional ratio 0.034%).

The apparatus thus completed was continuously operated for one month to distill the acrylic acid-containing liquid mentioned above. At the end of the continued operation, the effluent of distillation was found to have a maleic acid impurity concentration of 0.1 wt. %. When the interior of the column was inspected at the end of one month's continued operation, the polymer formed in the column was found to weigh about 2 kg.

(Controls 1–5)

The purification of an acrylic acid-containing solution was performed by following the procedure of Example 1 while omitting the installation of a vapor dispersing device in the re-boiler vapor inlet part. In this case, the lower end of the re-boiler vapor inlet part was 500 mm above the liquid level and 1,500 mm above the lowermost tray.

In this while, the concentration of impurity maleic acid in the effluent of distillation was 0.15 wt. %. When the interior of the column was inspected at the end of one month's continued operation, the polymer formed in the column was found to weigh about 10 kg.

Controls 2–5 were carried out under the conditions shown in Table 1 and the results were evaluated in the same manner as in Example 1. The results are shown in Table 1.

TABLE 1

|  |  | Example | Control 1 | Control 2 | Control 3 | Control 4 | Control 5 |
|---|---|---|---|---|---|---|---|
| Inner diameter of column | mm | 1300 | ← | ← | ← | ← | ← |
| Number of shelves |  | 35 | ← | ← | ← | ← | ← |
| Inside diameter of re-boiler vapor inlet | mm | 400 | ← | ← | ← | ← | ← |
| Working pressure | mmHg | 35 | ← | ← | ← | ← | ← |
| Working temperature | ° C. | 67 | ← | ← | ← | ← | ← |
| <Vapor dispersing device> |  |  |  |  |  |  |  |
| Vapor dispersing device |  | Equipped | None | Equipped | Equipped | Equipped | Equipped |
| Width | mm | 600 | — | 600 | ← | ← | ← |
| Length | mm | 400 | — | 400 | ← | ← | ← |
| Cross section ratio of column |  | 25% | — | 25% | ← | ← | ← |
| Distance from opening part to liquid level | mm | 500 | 500*[1] | 30 | 500 | 500 | 500 |
| Inside diameter ratio of re-boiler vapor inlet |  | 1.25 | 1.25 | 0.075 | 1.25 | 1.25 | 1.25 |
| Distance from opening part to lowermost tray | mm | 1500 | 1500*[2] | 1500 | 500 | 1500 | 1500 |
| Inside diameter ratio of re-boiler vapor inlet |  | 3.75 | 3.75 | 3.75 | 1.25 | 3.75 | 3.75 |
| Hole for releasing a vapor |  | Equipped | — | Equipped | None | None | Equipped |
| Diameter of hole for releasing a vapor | mm | 12 | — | 12 | ← | — | 12 |
| Number of hole for releasing a vapor | mm | 4 | — | 4 | ← | — | 4 |
| Area ratio of column |  | 0.034% | — | 0.034% | ← | — | 0.034% |
| Maleic acid in feed raw material | Weight % | 5 | ← | ← | ← | ← | ← |
| Polymerization inhibitor (phenothiazine) | ppm | 100 | ← | ← | ← | ← | ← |
| Introduction of oxygen |  | Equipped | Equipped | Equipped | Equipped | Equipped | None |
| <Results of one month's continued operation> |  |  |  |  |  |  |  |
| Maleic acid in distillate | Weight % | 0.1 | 0.15 | 0.13 | 0.13 | 0.11 | 0.1 |
| Polymer in column | kg | 2 | 10 | 2 | 2 | 2.3 | 3 |

*[1]: Distance from the lower end of re-boiler vapor inlet to the liquid level
*[2]: Distance from the lower end of re-boiler vapor inlet to the lowermost tray

What is claimed is:

1. A purifying apparatus comprising a vapor dispersing device positioned in a vapor inlet part of the purifying apparatus on a lateral inside thereof said vapor dispersing device having at least one opening part facing downward from a horizontal direction and a horizontal projected cross section area of the opening part in a range of 10–40% of a cross section area of said purifying apparatus, wherein the purifying apparatus is a plate tower or a packed tower and the distance from the opening part of the vapor dispersing device to a lowermost tray of the plate tower or a packing supporting member of the packed tower is in a range of 1.5–8 times a diameter of the vapor inlet part.

2. A purifying apparatus according to claim 1, wherein the distance from the opening part of the vapor dispersing device to a liquid level in the bottom part of the apparatus is in a range of 0.1–5 times a diameter of the vapor inlet part.

3. A purifying apparatus according to claim 1, wherein the apparatus is provided with not less than two vapor dispersing devices or the vapor dispersing device is provided with not less than two of the opening parts.

4. A purifying apparatus according to claim 1, wherein the vapor dispersing device is provided in an upper part thereof with a hole for releasing a vapor and the total hole area is in a range of 0.001–2% of the cross section area of the purifying apparatus.

5. A purifying apparatus according to claim 1, wherein said apparatus receives an easily polymerizable compound and said apparatus is used for distilling said easily polymerizable compound.

6. A purifying apparatus according to claim 5, wherein the easily polymerizable compound is (meth)acrylic acid and/or an ester thereof.

7. The apparatus of claim 1, wherein said vapor dispersing device has an arc shape.

8. The apparatus of claim 1 wherein said vapor dispersing device has a triangular shape.

9. The apparatus of claim 1, wherein said vapor dispersing device has a shape of a nozzle.

10. The apparatus of claim 9, wherein said vapor dispersing device has a plurality of said opening parts.

11. A purifying apparatus having a distillation column and a re-boiler disposed outside the column, said apparatus comprising a vapor outlet nozzle connected from the re-boiler to a column side wall in a gas phase part of a bottom of the distillation column and a vapor dispersing device having an upper part thereof formed as elongated from the part at which the vapor outlet nozzle connects to said column side wall, said vapor dispersing device having an opening part facing downward from a horizontal direction and a horizontal projected cross section area in a range of 10–40% of a cross section area of said apparatus, wherein said vapor dispersing device deflects downwardly vapor introduced from the re-boiler and said distillation column is a plate tower or a packed tower and the distance from the opening part of the vapor dispersing device to a lowermost tray of the plate tower or a packing supporting member of the packed tower is in a range of 1.5–8 times a diameter of a vapor inlet part.

12. A purifying apparatus according to claim 11, wherein the distillation column comprises a molecular oxygen supplying part.

* * * * *